US012793185B2

(12) United States Patent
Hamauzu

(10) Patent No.: US 12,793,185 B2
(45) Date of Patent: Nov. 10, 2026

(54) RADIATION IMAGE PROCESSING DEVICE, RADIATION IMAGE PROCESSING METHOD, AND RADIATION IMAGE PROCESSING PROGRAM

(71) Applicant: FUJIFILM CORPORATION, Tokyo (JP)

(72) Inventor: Shin Hamauzu, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 233 days.

(21) Appl. No.: 18/795,201

(22) Filed: Aug. 6, 2024

(65) Prior Publication Data

US 2025/0078217 A1 Mar. 6, 2025

(30) Foreign Application Priority Data

Aug. 30, 2023 (JP) ................................ 2023-140234

(51) Int. Cl.

*G06T 5/70* (2024.01)
*A61B 6/00* (2024.01)
*G06T 5/50* (2006.01)

(52) U.S. Cl.

CPC ................ *G06T 5/70* (2024.01); *A61B 6/481* (2013.01); *A61B 6/5282* (2013.01); *G06T 5/50* (2013.01); *G06T 2207/10116* (2013.01); *G06T 2207/20224* (2013.01); *G06T 2207/30101* (2013.01)

(58) Field of Classification Search

CPC ... G06T 5/70; G06T 5/50; G06T 2207/10116; G06T 2207/20224; G06T 2207/30101; A61B 6/481; A61B 6/5282; A61B 6/504; A61B 6/5235

See application file for complete search history.

(56) References Cited

U.S. PATENT DOCUMENTS

| | | | | |
|---|---|---|---|---|
| 10,229,515 B2 * | 3/2019 | Ohishi | .................. | A61B 6/032 |
| 10,610,180 B2 * | 4/2020 | Ashida | .................. | A61B 6/032 |
| 12,279,903 B2 * | 4/2025 | Takahashi | ............ | A61B 6/4241 |
| 2012/0243759 A1 * | 9/2012 | Fujisawa | ................ | A61B 6/032 378/19 |
| 2013/0010924 A1 * | 1/2013 | Ohishi | .................. | A61B 6/022 378/42 |

(Continued)

FOREIGN PATENT DOCUMENTS

| | | |
|---|---|---|
| JP | 2014-207958 A | 11/2014 |
| JP | 2015-043959 A | 3/2015 |
| JP | 2020-501692 A | 1/2020 |

*Primary Examiner* — Lewis G West

(74) *Attorney, Agent, or Firm* — SOLARIS Intellectual Property Group, PLLC

(57) ABSTRACT

A processor is configured to: acquire a first radiation image including a tubular structure before an injection of a contrast agent and a second radiation image including the tubular structure during the injection of the contrast agent or after the injection of the contrast agent; derive a processed first radiation image by removing a scattered ray component included in the first radiation image; derive a processed second radiation image by removing a scattered ray component included in the second radiation image based on the scattered ray component of the first radiation image; and derive a difference image between the processed first radiation image and the processed second radiation image.

10 Claims, 5 Drawing Sheets

(56) References Cited

U.S. PATENT DOCUMENTS

| | | | | |
|---|---|---|---|---|
| 2015/0325011 | A1* | 11/2015 | Ashida | A61B 6/032 382/131 |
| 2015/0379711 | A1 | 12/2015 | Imai | |
| 2016/0081648 | A1* | 3/2016 | Tajima | A61B 6/4291 378/165 |
| 2016/0093030 | A1* | 3/2016 | Naito | A61B 6/5205 382/132 |
| 2016/0140720 | A1 | 5/2016 | Naito | |
| 2016/0232661 | A1* | 8/2016 | Ohishi | A61B 6/032 |
| 2017/0221207 | A1 | 8/2017 | Imai | |
| 2018/0122094 | A1 | 5/2018 | Naito | |
| 2020/0093449 | A1 | 3/2020 | Rouet et al. | |
| 2021/0186444 | A1 | 6/2021 | Rouet et al. | |
| 2022/0287663 | A1* | 9/2022 | Taki | G06T 7/0012 |
| 2022/0287664 | A1* | 9/2022 | Taki | A61B 6/4241 |
| 2023/0394639 | A1* | 12/2023 | Taki | G06T 5/50 |
| 2023/0404510 | A1* | 12/2023 | Taki | A61B 6/482 |
| 2026/0083421 | A1* | 3/2026 | Takahashi | A61B 6/482 |

* cited by examiner

RADIATION IMAGE PROCESSING DEVICE, RADIATION IMAGE PROCESSING METHOD, AND RADIATION IMAGE PROCESSING PROGRAM

CROSS REFERENCE TO RELATED APPLICATIONS

The present application claims priority from Japanese Patent Application No. 2023-140234, filed on Aug. 30, 2023, the entire disclosure of which is incorporated herein by reference.

BACKGROUND

Technical Field

The present disclosure relates to a radiation image processing device, a radiation image processing method, and a radiation image processing program.

Related Art

In the related art, a contrast radiation image diagnostic apparatus has been used to examine a shape of a blood vessel, an abnormality of a blood vessel, a blood flow state, and the like, and perform treatment thereof. The contrast radiation image diagnostic apparatus is called an angiography apparatus. In the angiography apparatus, a contrast agent is injected into the blood vessel using a catheter, and a digital subtraction angiography (DSA) image, which is a difference image between an image (mask image) before the injection of the contrast agent and an image (live image) during the injection of the contrast agent or after the injection of the contrast agent, is acquired. In the DSA image, a structure other than a region in which the contrast agent is injected is removed. Therefore, by using the DSA image, a doctor can efficiently perform the examination and the treatment of the blood vessel while checking a distribution of the blood flow in the blood vessel and a state of the blood vessel, such as the stenosis of the blood vessel.

Meanwhile, since the mask image and the live image are acquired at different timings, a motion artifact based on a body movement may occur in the DSA image. Therefore, a method of reducing the motion artifact has been proposed (see JP2020-501692A).

In the DSA image, the state of the blood vessel can be checked based on the region of the contrast agent injected into the blood vessel. However, due to an influence of scattered rays generated in a case in which radiation is transmitted through a subject, an unnecessary structure for observation, such as a bone that overlaps with the contrast agent in the subject, may not be completely removed by the difference, and may be included in the DSA image. Such an unnecessary structure hinders the check of the state of the blood vessel.

SUMMARY OF THE INVENTION

The present disclosure has been made in view of the above circumstances, and an object of the present disclosure is to suppress an unnecessary structure that hinders observation of a tubular structure, such as a blood vessel, in a difference image such as a DSA image.

The present disclosure relates to a radiation image processing device comprising: at least one processor, in which the processor is configured to: acquire a first radiation image including a tubular structure before an injection of a contrast agent and a second radiation image including the tubular structure during the injection of the contrast agent or after the injection of the contrast agent; derive a processed first radiation image by removing a scattered ray component included in the first radiation image; derive a processed second radiation image by removing a scattered ray component included in the second radiation image based on the scattered ray component of the first radiation image; and derive a difference image between the processed first radiation image and the processed second radiation image.

It should be noted that, in the radiation image processing device according to the present disclosure, the processor may be configured to: extract a region of the contrast agent from the second radiation image; derive, for the region of the contrast agent in the second radiation image, the scattered ray component of the second radiation image by correcting a scattered ray component of a first region in the first radiation image corresponding to the region of the contrast agent; derive, for other regions other than the region of the contrast agent in the second radiation image, the scattered ray component of a second region in the first radiation image corresponding to the other regions, as the scattered ray component of the second radiation image; and derive the processed second radiation image by removing the derived scattered ray component of the second radiation image from the second radiation image.

In the radiation image processing device according to the present disclosure, the processor may be configured to derive, for the region of the contrast agent in the second radiation image, the scattered ray component of the second radiation image by correcting the scattered ray component of the first region based on an amount and a density of the contrast agent injected into the tubular structure.

In the radiation image processing device according to the present disclosure, the processor may be configured to derive, for the region of the contrast agent in the second radiation image, the scattered ray component included in the second radiation image by correcting the scattered ray component of the first region based on a pixel value of the first region.

In the radiation image processing device according to the present disclosure, the tubular structure may be a blood vessel.

The present disclosure relates to a radiation image processing method comprising: via a computer, acquiring a first radiation image including a tubular structure before an injection of a contrast agent and a second radiation image including the tubular structure during the injection of the contrast agent or after the injection of the contrast agent; deriving a processed first radiation image by removing a scattered ray component included in the first radiation image; deriving a processed second radiation image by removing a scattered ray component included in the second radiation image based on the scattered ray component of the first radiation image; and deriving a difference image between the processed first radiation image and the processed second radiation image.

The present disclosure relates to a radiation image processing program causing a computer to execute: a procedure of acquiring a first radiation image including a tubular structure before an injection of a contrast agent and a second radiation image including the tubular structure during the injection of the contrast agent or after the injection of the contrast agent; a procedure of deriving a processed first radiation image by removing a scattered ray component included in the first radiation image; a procedure of deriving a processed second radiation image by removing a scattered ray component included in the second radiation image based on the scattered ray component of the first radiation image; and a procedure of deriving a difference image between the processed first radiation image and the processed second radiation image.

According to the present disclosure, it is possible to suppress the unnecessary structure that hinders the observation of the tubular structure, such as the blood vessel, in the difference image such as the DSA image.

DETAILED DESCRIPTION

Figure 1:
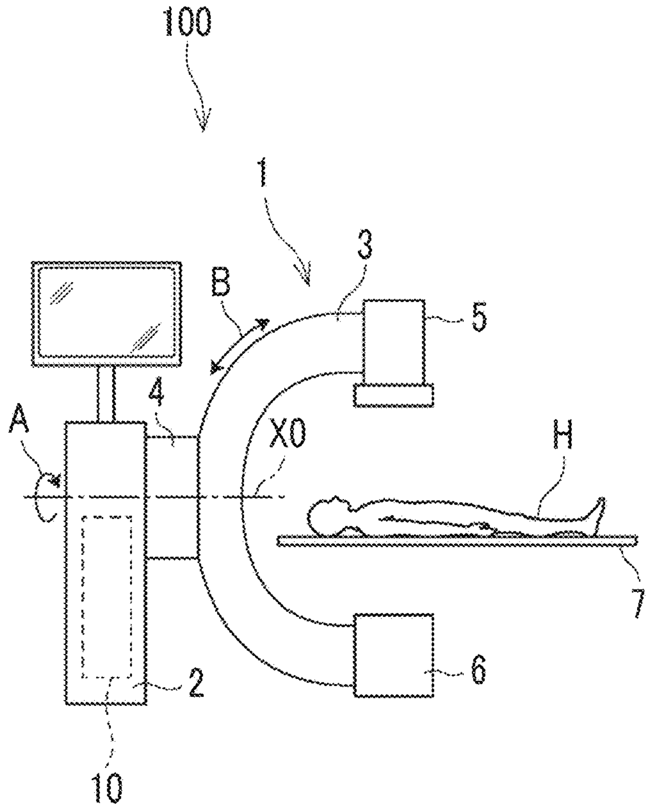
FIG. 1 is a diagram showing an outline of an angiography system to which a radiation image processing device according to an embodiment of the present disclosure is applied.

In the following description, an embodiment of the present disclosure will be described with reference to the drawings. FIG. 1 is a schematic block diagram showing a configuration of an angiography system to which a radiation image processing device according to the embodiment of the present disclosure is applied. As shown in FIG. 1, an angiography system 100 according to the present embodiment comprises an angiography apparatus 1 and a radiation image processing device 10 according to the present embodiment.

The angiography apparatus 1 is an apparatus for examining a shape of a blood vessel of a subject, an abnormality of the blood vessel, a state of blood flow, and the like, and performing the treatment thereof. In the present embodiment, the angiography apparatus 1 is used to perform the examination and the treatment of, for example, an aorta and an artery branched from the aorta. The angiography apparatus 1 includes a C-arm 3 that is attached to a body 2 by an attachment portion 4 to be rotatable around an axis X0, that is, in a direction of an arrow A. In addition, the C-arm 3 is attached to the attachment portion 4 to be movable in a direction of an arrow B shown in FIG. 1. A radiation source 5 is attached to one end part of the C-arm 3, and an imaging unit 6 is attached to the other end part of the C-arm 3. The imaging unit 6 is provided with a radiation detector that detects radiation transmitted through a subject H on an imaging table 7 to generate a radiation image of the subject H. The body 2 includes a radiation image processing device 10 according to the present embodiment. The blood vessel is an example of a tubular structure.

In the present embodiment, the blood vessel is imaged by injecting a contrast agent. First, the subject H is imaged before the contrast agent is injected, to acquire a radiation image (hereinafter, referred to as a mask image) of the subject H before the contrast agent is injected. The subject H is imaged during the injection of the contrast agent or after the injection of the contrast agent, to acquire a radiation image (hereinafter, referred to as a live image) of the subject H during the injection of the contrast agent or after the injection of the contrast agent. The mask image is an example of a first radiation image, and the live image is an example of a second radiation image.

Figure 2:
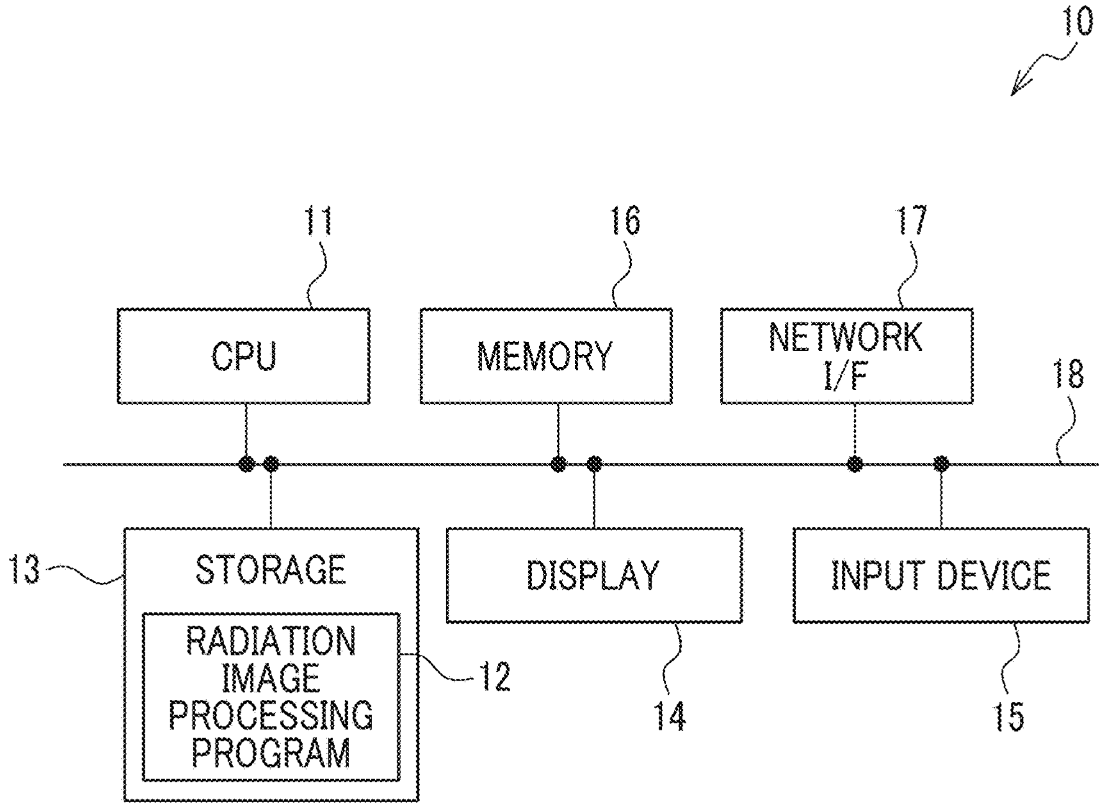
FIG. 2 is a diagram showing a schematic configuration of the radiation image processing device according to the present embodiment.

Next, the radiation image processing device according to the present embodiment will be described. First, a hardware configuration of the radiation image processing device according to the present embodiment will be described with reference to FIG. 2. As shown in FIG. 2, the radiation image processing device 10 is a computer, such as a workstation, a server computer, and a personal computer, and comprises a central processing unit (CPU) 11, a non-volatile storage 13, and a memory 16 as a transitory storage region. In addition, the radiation image processing device 10 comprises a display 14 such as a liquid crystal display, an input device 15 such as a keyboard and a mouse, and a network interface (I/F) 17 connected to a network and the imaging unit 6. The CPU 11, the storage 13, the display 14, the input device 15, the memory 16, and the network I/F 17 are connected to a bus 18. It should be noted that the CPU 11 is an example of a processor according to the present disclosure.

The storage 13 is realized by a hard disk drive (HDD), a solid state drive (SSD), a flash memory, and the like. A radiation image processing program 12 installed in the radiation image processing device 10 is stored in the storage 13 as a storage medium. The CPU 11 reads out the radiation image processing program 12 from the storage 13, expands the read out radiation image processing program 12 to the memory 16, and executes the expanded radiation image processing program 12.

It should be noted that the radiation image processing program 12 is stored in a storage device of the server computer connected to the network or in a network storage in a state of being accessible from the outside, and is downloaded and installed in the computer that configures the radiation image processing device 10 in response to the request. Alternatively, the radiation image processing program 12 is distributed in a state of being recorded on a recording medium, such as a digital versatile disc (DVD) or a compact disc read only memory (CD-ROM), and is installed in the computer that configures the radiation image processing device 10 from the recording medium.

Figure 3:
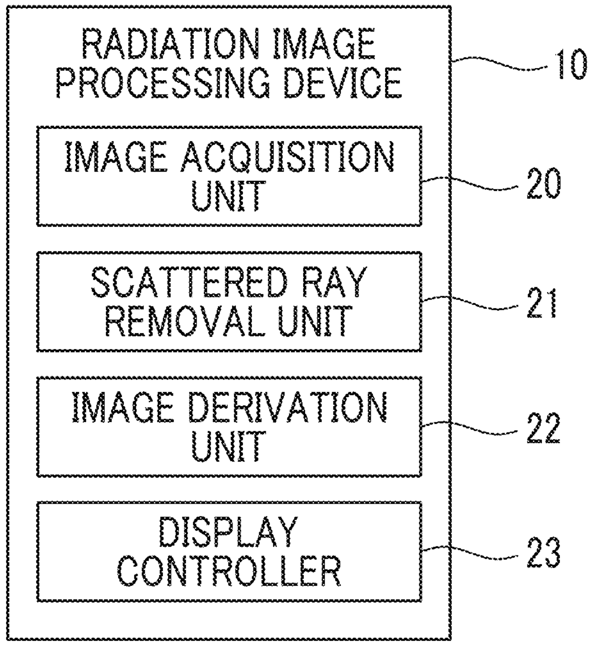
FIG. 3 is a diagram showing a functional configuration of the radiation image processing device according to the present embodiment.

Then, a functional configuration of the radiation image processing device according to the present embodiment will be described. FIG. 3 is a diagram showing the functional configuration of the radiation image processing device according to the present embodiment. The radiation image processing device 10 comprises, as shown in FIG. 3, an image acquisition unit 20, a scattered ray removal unit 21, an image derivation unit 22, and a display controller 23. In a case in which the CPU 11 executes the radiation image processing program 12, the CPU 11 functions as the image acquisition unit 20, the scattered ray removal unit 21, the image derivation unit 22, and the display controller 23.

The image acquisition unit 20 acquires a mask image G1 and a live image G2 by causing the angiography apparatus 1 to image the subject H. In a case of the imaging, imaging conditions such as an irradiation dose of the radiation, a tube voltage, and a source-to-image receptor distance (SID) (distance between an X-ray tube focus and an image receiving surface) are set. The set imaging conditions are stored in the storage 13.

It should be noted that the mask image G1 and the live image G2 may be acquired by a program separate from the radiation image processing program according to the present embodiment. In this case, the mask image G1 and the live image G2 are stored in the storage 13, and the image acquisition unit 20 reads out the mask image G1 and the live image G2 stored in the storage 13 from the storage 13, for processing.

Here, in a case of imaging the subject H using the angiography apparatus 1, since the scattered rays are generated in a case in which the radiation passes through the subject H, a scattered ray component caused by the scattered rays is included in the mask image G1 and the live image G2. The mask image G1 is acquired before the injection of the contrast agent, but the live image G2 is acquired during the injection of the contrast agent or after the injection of the contrast agent. Since the contrast agent absorbs the radiation, the scattered ray component of the radiation is also absorbed by the contrast agent. As a result, the scattered ray component included in a blood vessel region into which the contrast agent is injected on the live image G2 is less than the scattered ray component of a blood vessel region on the mask image G1.

In a situation in which the scattered ray components included in this way are different, in a case in which the same scattered ray removal processing is performed on the mask image G1 and the live image G2, a degree of removal of the scattered ray component in the blood vessel region into which the contrast agent is injected is different between the mask image G1 and the live image G2. Accordingly, the contrast of the blood vessel region is different between the mask image G1 and the live image G2. As a result, in a case in which the DSA image, which is a difference image between the mask image G1 from which the scattered ray component is removed and the live image G2 from which the scattered ray component is removed, is derived as described later, an unnecessary structure such as a bone overlaps with a blood vessel into which the contrast agent is injected, may not be completely removed, and may remain in the DSA image. Such an unnecessary structure hinders the check of the state of the blood vessel.

In the present embodiment, the scattered ray removal unit 21 derives the scattered ray component of each of the mask image G1 and the live image G2, and removes the scattered ray components of the mask image G1 and the live image G2. In this case, in the present embodiment, the scattered ray component of the live image G2 is removed based on the scattered ray component of the mask image G1. First, the description of the removal of the scattered ray component from the mask image G1 will be made.

In the present embodiment, the scattered ray component is removed from the mask image G1 by using, for example, methods disclosed in JP2014-207958A, JP2015-043959A, and the like. It should be noted that the method of removing the scattered ray component is not limited thereto, and any method can be used. Hereinafter, scattered ray removal processing in a case in which the method disclosed in JP2015-043959A is used will be described. In a case in which a method disclosed in JP2015-043959A or the like is used, the derivation of a body thickness distribution of the subject H and the derivation of the scattered ray component for removing the scattered ray component are performed at the same time.

It should be noted that, in a case of removing the scattered ray component, a low-frequency image representing a low-frequency component of the mask image G1 and the live image G2 may be generated to derive the body thickness distribution by using the low-frequency image.

First, the scattered ray removal unit 21 acquires a virtual model K1 of the subject H having an initial body thickness distribution Ts(x,y). The virtual model K1 is data virtually representing the subject H of which the body thickness in accordance with the initial body thickness distribution Ts(x, y) is associated with a coordinate position of each pixel of the mask image G1. It should be noted that the virtual model K1 of the subject H having the initial body thickness distribution Ts(x,y) is stored in the storage 13 in advance, but the virtual model K1 may be acquired from an external server in which the virtual model K1 is stored.

Next, as shown in Expression (1) and Expression (2), the scattered ray removal unit 21 derives an estimation primary ray image Ip(x,y) obtained by estimating a primary ray image obtained by imaging the virtual model K1 and an estimation scattered ray image Is(x,y) obtained by estimating a scattered ray image obtained by imaging the virtual model K1, based on the virtual model K1. Further, as shown in Expression (3), the scattered ray removal unit 21 derives an image obtained by combining the estimation primary ray image Ip(x,y) and the estimation scattered ray image Is(x,y) as an estimation image Im(x,y) in which the mask image G1 obtained by imaging the subject H is estimated.

$$Ip(x, y) = Io(x, y) \times \exp(-\mu ls \times T(x, y)) \quad (1)$$

$$Is(x, y) = Io(x, y) * S\sigma(T(x, y)) \quad (2)$$

$$Im(x, y) = Is(x, y) + Ip(x, y) \quad (3)$$

Here, (x,y) is coordinates of the pixel position of the mask image G1, Ip(x,y) is a primary ray component at the pixel position (x,y), Is(x,y) is the scattered ray component at the pixel position (x,y), Io(x,y) is an incident dose on the surface of the subject H at the pixel position (x,y), μls is an attenuation coefficient of the subject H, and Sσ(T(x,y)) is a convolution kernel representing the characteristics of the scattering according to the body thickness distribution T(x, y) of the subject H at the pixel position (x,y). It should be noted that, in a case of deriving the first estimation image Im(x,y), the initial body thickness distribution Ts(x,y) is used as the body thickness distribution T(x,y) in Expression (1) and Expression (2). Expression (1) is based on a known exponential attenuation law, and Expression (2) is based on a method described in "J M Boon et al, An analytical model of the scattered radiation distribution in diagnostic radiology, Med. Phys. 15 (5), September/October 1988 (Reference 1). It should be noted that the incident dose Io(x,y) on the surface of the subject H is the irradiation dose that is derived based on the imaging conditions. In addition, the attenuation coefficient μls of the subject H in Expression (1) is an attenuation coefficient of a soft tissue for a low-energy image of the subject H.

Further, * in Expression (2) is an operator indicating a convolution operation. The properties of the kernel also change depending on a distribution of an irradiation field in the angiography apparatus 1 (in a case in which an irradiation field stop is used), a distribution of a composition of the subject H, the irradiation dose during the imaging, the tube voltage, the imaging distance, the characteristics of the radiation detector used in the imaging unit 6, and the like, in addition to the body thickness of the subject H. According to the method described in Reference 1, the scattered rays can be approximated by convolution of a point spread function ($S\sigma(T(x,y))$ in Expression (3)) with respect to the primary rays. It should be noted that $S\sigma(T(x,y))$ can be experimentally calculated according to, for example, the irradiation field information, the subject information, and the imaging conditions.

In the present embodiment, $S\sigma(T(x,y))$ may be calculated based on the irradiation field information, the subject information, and the imaging conditions during the imaging. However, a table in which various types of irradiation field information, various types of subject information, and various imaging conditions are associated with $S\sigma(T(x,y))$ may be stored in the storage 13, and $S\sigma(T(x,y))$ may be calculated based on the irradiation field information, the subject information, and the imaging conditions during the imaging with reference to this table. It should be noted that $S\sigma(T(x,y))$ may be approximated by T(x,y).

Next, the scattered ray removal unit 21 corrects the initial body thickness distribution Ts(x,y) of the virtual model K1 such that a difference between the estimation image Im and the mask image G1 is reduced. The scattered ray removal unit 21 repeats the generation of the estimation image Im using the corrected body thickness distribution T(x,y) and the correction of the body thickness distribution T(x,y) until the difference between the estimation image Im and the mask image G1 satisfies a predetermined termination condition. The scattered ray removal unit 21 subtracts the scattered ray component Is(x,y) derived by Expression (2) in a case in which the termination condition is satisfied from the mask image G1. It should be noted that the scattered ray component derived for the mask image G1 will be referred to as a scattered ray component Is1(*x,y*) in the following description. Accordingly, the scattered ray component included in the mask image G1 is removed. G11 is used as a reference numeral of a processed mask image from which the scattered ray component is removed.

Next, the description of the removal of the scattered ray component from the live image G2 will be made. First, the scattered ray removal unit 21 derives a scattered ray component Is2(*x,y*) of the live image G2 based on the scattered ray component (x,y) of the mask image G1. Therefore, the scattered ray removal unit 21 extracts a region A0 of the contrast agent from the live image G2. Here, in the live image G2, the region of the contrast agent has a higher brightness (lower density) than other regions other than the region of the contrast agent. Therefore, the scattered ray removal unit 21 extracts the region A0 of the contrast agent from the live image G2 via threshold value processing. It should be noted that the region A0 of the contrast agent may be extracted from the live image G2 by using a trained model that has been trained through machine learning to extract the region A0 of the contrast agent from the radiation image.

The scattered ray removal unit 21 derives, for the region A0 of the contrast agent extracted from the live image G2, the scattered ray component Is2(*x,y*) by correcting the scattered ray component Is1(*x,y*) of a first region A1 in the mask image G1 corresponding to the region of the contrast agent based on the amount and the density of the contrast agent injected into the blood vessel. Specifically, as shown in Expression (4), the scattered ray component Is2(*x,y*) is derived by multiplying the scattered ray component Is1(*x,y*) of the first region A1 in the mask image G1 by a correction coefficient α1.

Figure 4:
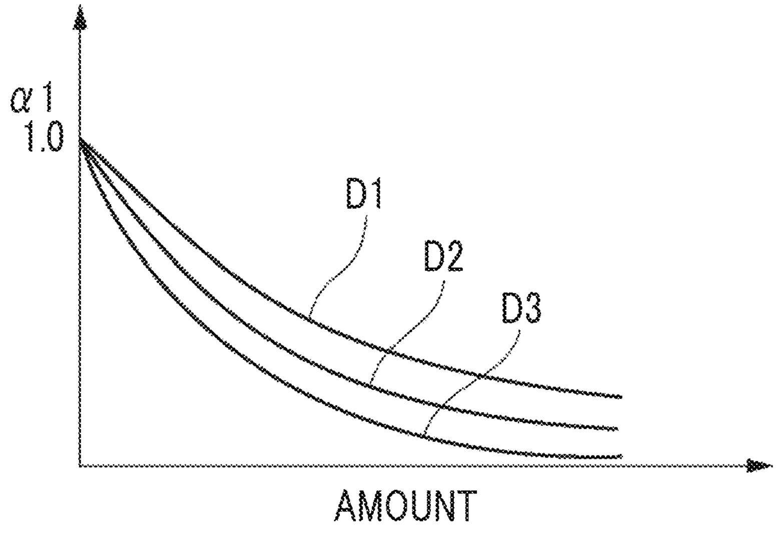
FIG. 4 is a diagram showing a correction coefficient according to an amount and a density of a contrast agent.

The correction coefficient α1 has a value equal to or less than 1, which is determined by, for example, the amount and the density of the contrast agent, as shown in FIG. 4. FIG. 4 shows a relationship between the amount of the contrast agent and the correction coefficient α1, for three types of densities D1 to D3 (D1<D2<D3). As shown in FIG. 4, the correction coefficient α1 has a value such that the value is smaller than 1.0 as the density and the amount of the contrast agent are higher. It should be noted that the value of the correction coefficient α1 also varies depending on the type of the contrast agent.

$$Is2(x, y) = Is1(x, y)\times\alpha 1 \tag{4}$$

On the other hand, the scattered ray removal unit 21 derives, for the other regions of the live image G2 other than the region A0 of the contrast agent, the scattered ray component Is1(*x,y*) derived from a second region A2 in the mask image G1 corresponding to the other regions, as the scattered ray component Is2(*x,y*) of the live image G2 as it is.

The scattered ray removal unit 21 derives a processed live image G22 from which the scattered ray component is removed, by subtracting the derived scattered ray component Is2(*x,y*) from the live image G2.

As shown in Expression (5), the image derivation unit 22 derives a difference image in which the blood vessel region in the subject H into which the contrast agent is injected is emphasized, that is, a DSA image Gp by subtracting the processed mask image G11 from the processed live image G22.

$$Gp(x, y) = G22(x, y) - G11(x, y) \tag{5}$$

The display controller 23 displays the DSA image Gp on the display 14. The doctor performs the examination and the treatment of the blood vessel while viewing the DSA image Gp displayed on the display.

Figure 5:
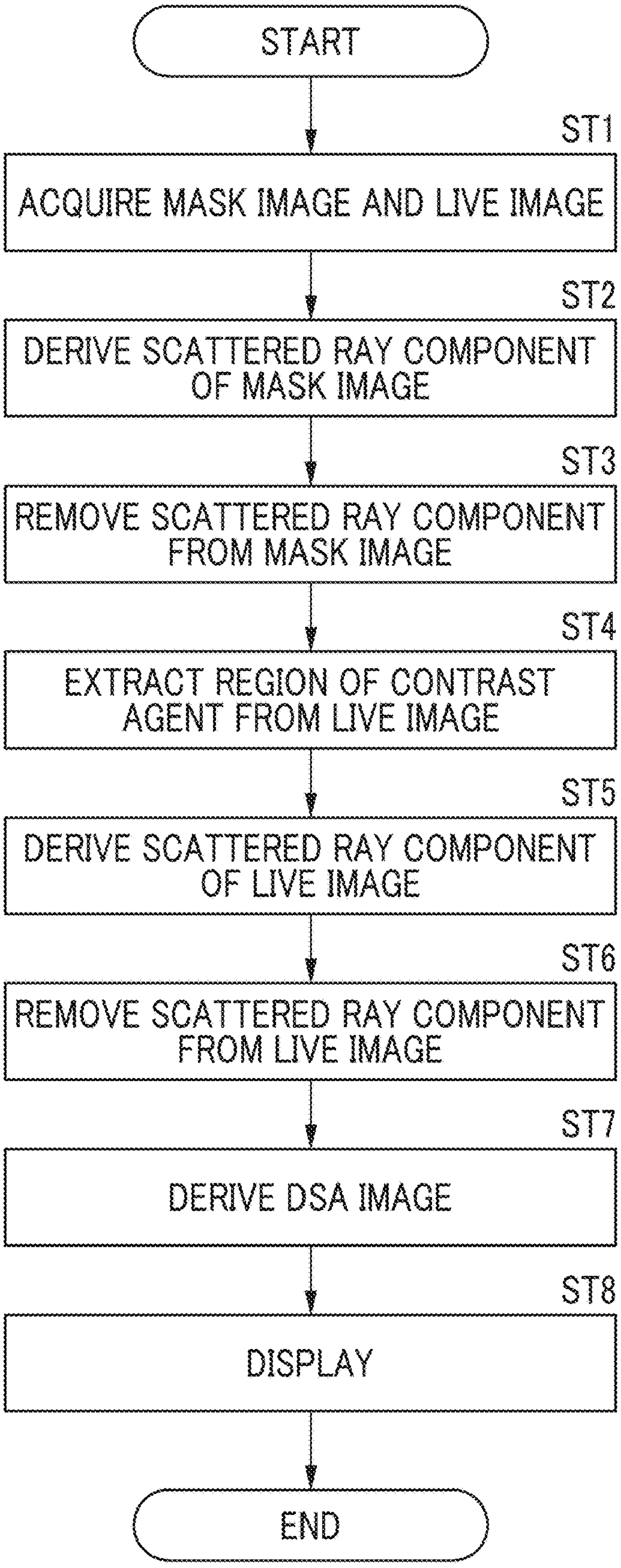
FIG. 5 is a flowchart showing processing performed in the present embodiment.
Figure 6:
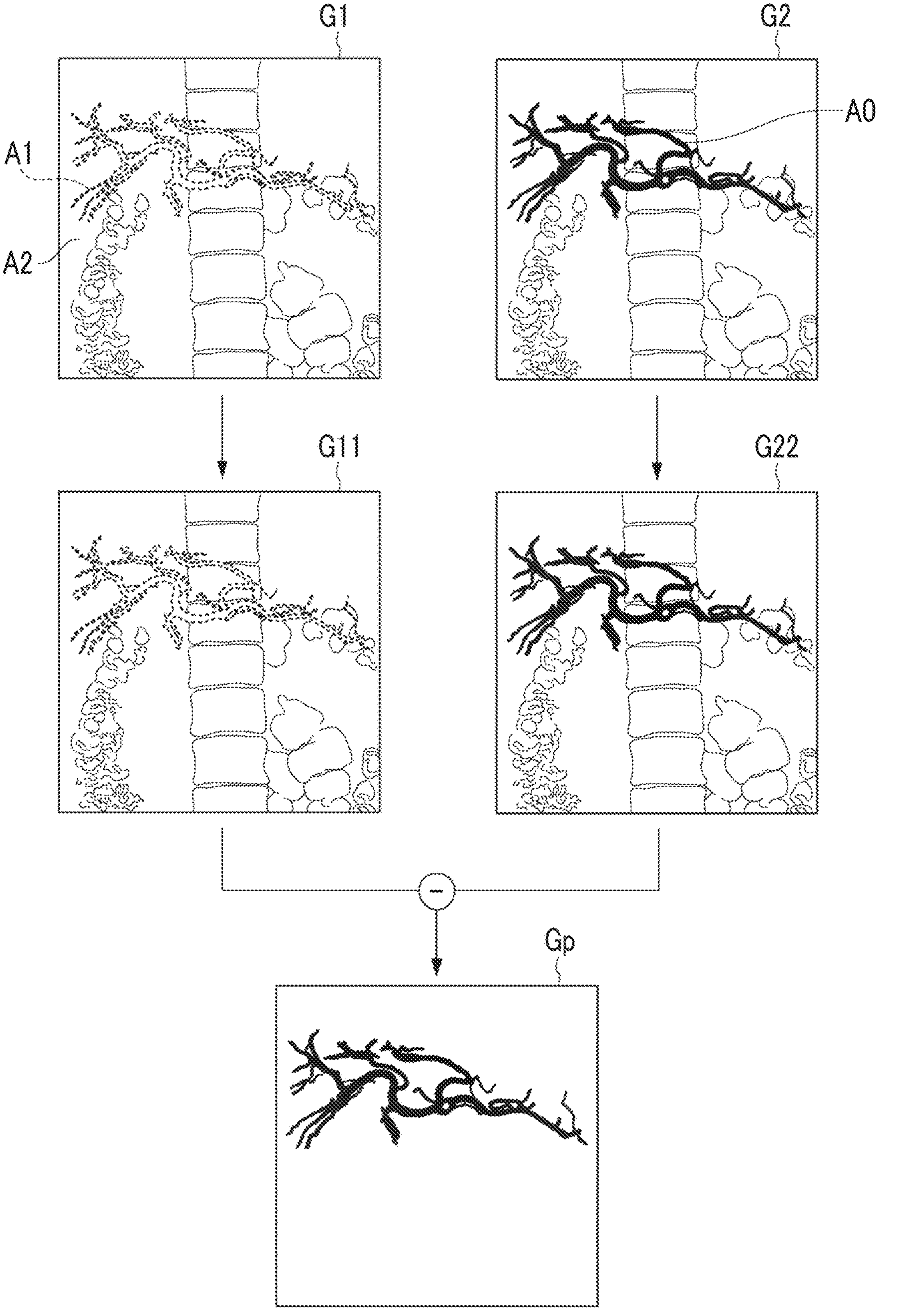
FIG. 6 is a conceptual diagram of the processing performed in the present embodiment.

Then, processing performed in the present embodiment will be described. FIG. 5 is a flowchart showing processing performed in the present embodiment, and FIG. 6 is a conceptual diagram of the processing performed in the present embodiment. It should be noted that it is assumed that the mask image G1 and the live image G2 are acquired by the imaging, and are stored in the storage 13.

In a case in which an instruction to start the processing is input from the input device 15, the image acquisition unit 20 acquires the mask image G1 and the live image G2 from the storage 13 (step ST1). Then, the scattered ray removal unit 21 derives the scattered ray component Is1 included in the mask image G1 (step ST2), and derives the processed mask image G11 by removing the scattered ray component of the mask image G1 by subtracting the derived scattered ray component Is1 from the mask image G1 (step ST3).

Then, the scattered ray removal unit 21 extracts the region A0 of the contrast agent from the live image G2 (step ST4). The scattered ray removal unit 21 derives the scattered ray component for the live image G2 (step ST5).

That is, for the region A0 of the contrast agent in the live image G2, the scattered ray component Is2(*x,y*) is derived by correcting the scattered ray component Is1(*x,y*) of the first region A1 in the mask image G1 corresponding to the region of the contrast agent as shown in Expression (4). For the other regions of the live image G2 other than the region A0 of the contrast agent, the scattered ray component Is1(*x,y*) of the second region A2 in the mask image G1 corresponding to the other regions is derived as it is as the scattered ray component Is2(x,y).

The scattered ray removal unit 21 derives the processed live image G22 by subtracting the derived scattered ray component Is2(x,y) from the live image G2 (step ST6). Then, the image derivation unit 22 derives the DSA image Gp by subtracting the processed mask image G11 from the processed live image G22 (step ST7). The display controller 23 displays the DSA image Gp on the display 14 (step ST8), and terminates the processing.

In this way, in the present embodiment, the scattered ray component included in the live image G2 is removed based on the scattered ray component of the mask image G1. Therefore, in the region of the contrast agent, the scattered ray component can be accurately removed from the live image. Therefore, according to the present embodiment, in a case in which the difference image, such as the DSA image, is derived, it is possible to suppress the structure, such as the bone that overlaps with the contrast agent in the region of the contrast agent, from remaining, and thus it is possible to prevent the unnecessary structure from hindering the check of the state of the blood vessel.

In particular, in the present embodiment, the scattered ray component Is2(x,y) of the contrast agent region A0 in the live image G2 is derived by correcting the scattered ray component Is1(x,y) of the first region A1 in the mask image G1. Accordingly, even in a case in which the scattered ray components are different between the mask image G1 and the live image G2 due to the influence of the contrast agent, the scattered ray component can be appropriately removed from each of the mask image G1 and the live image G2 by taking the difference into consideration. Therefore, it is possible to reliably prevent the unnecessary structure from remaining in the region of the contrast agent of the DSA image.

It should be noted that, in the embodiment described above, for the region of the contrast agent in the live image G2, the scattered ray component Is2(x,y) is derived by correcting the scattered ray component Is1(x,y) in the first region A1 in the mask image G1 based on the density and the amount of the contrast agent, but the present disclosure is not limited to this. The scattered ray component Is2(x,y) of the live image G2 may be derived by correcting the scattered ray component Is1(x,y) of the mask image G1 based on the pixel value of the first region A1 in the mask image G1.

Figure 7:
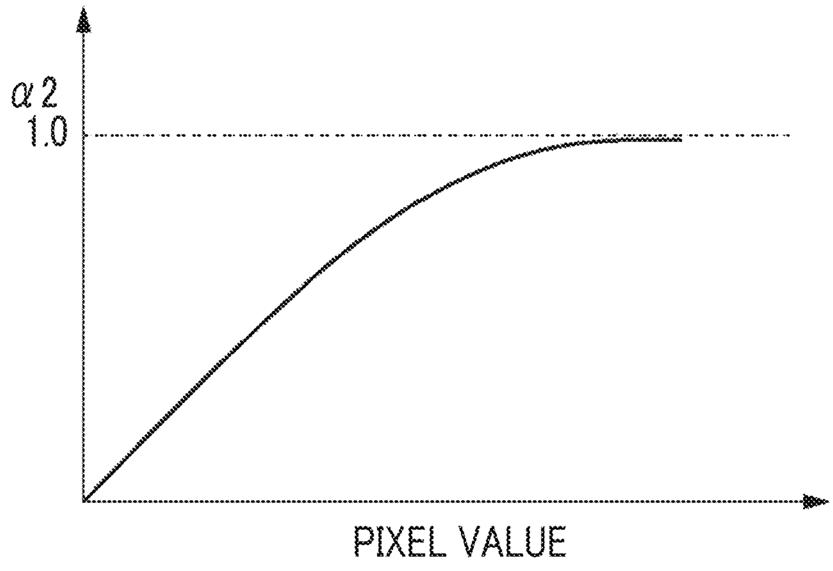
FIG. 7 is a diagram showing a correction coefficient according to a pixel value of a first radiation image.

Here, since the contrast agent absorbs the radiation, as the degree of absorption is larger, the pixel value is smaller and thus the density is lower (brightness is higher). Therefore, as shown in FIG. 7, by deriving a relationship between the pixel value and a correction coefficient α2 in advance such that the value approaches 1.0 as the pixel value is larger, the scattered ray component Is2(x,y) of the live image G2 may be derived by correcting the scattered ray component Is1(x, y) of the mask image G1 as shown in Expression (6).

$$Is2(x, y) = Is1(x, y) \times \alpha 2 \tag{6}$$

In addition, the radiation in the embodiment described above is not particularly limited, and α-rays or γ-rays can be applied in addition to X-rays.

In addition, in the embodiment described above, the blood vessel is used as the tubular structure, but the present disclosure is not limited to this. Any tubular structure that is subjected to the examination using the contrast agent, such as an esophagus and a large intestine, can be targeted.

In addition, in the embodiment described above, various processors shown below can be used as the hardware structure of the processing unit that executes various pieces of processing, such as the image acquisition unit 20, the scattered ray removal unit 21, the image derivation unit 22, and the display controller 23. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electrical circuit that is a processor having a circuit configuration which is designed for exclusive use in order to execute a specific processing, such as an application specific integrated circuit (ASIC).

One processing unit may be configured by one of these various processors, or may be configured by a combination of two or more processors of the same type or different types (for example, a combination of a plurality of FPGAs or a combination of the CPU and the FPGA). In addition, a plurality of processing units may be configured by one processor.

As an example of configuring the plurality of processing units by one processor, first, as represented by a computer of a client, a server, and the like there is an aspect in which one processor is configured by a combination of one or more CPUs and software and this processor functions as the plurality of processing units. Second, as represented by a system on a chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Further, as the hardware structures of these various processors, more specifically, it is possible to use an electrical circuit (circuitry) in which circuit elements, such as semiconductor elements, are combined.

What is claimed is:

1. A radiation image processing device comprising:

at least one processor, wherein the processor is configured to:

acquire a first radiation image including a tubular structure before an injection of a contrast agent and a second radiation image including the tubular structure during the injection of the contrast agent or after the injection of the contrast agent;

derive a processed first radiation image by removing a scattered ray component included in the first radiation image;

derive a processed second radiation image by removing a scattered ray component included in the second radiation image based on the scattered ray component of the first radiation image; and derive a difference image between the processed first radiation image and the processed second radiation image.

2. The radiation image processing device according to claim 1, wherein the processor is configured to:

extract a region of the contrast agent from the second radiation image;

derive, for the region of the contrast agent in the second radiation image, the scattered ray component of the second radiation image by correcting a scattered ray component of a first region in the first radiation image corresponding to the region of the contrast agent;

derive, for other regions other than the region of the contrast agent in the second radiation image, the scattered ray component of a second region in the first radiation image corresponding to the other regions, as the scattered ray component of the second radiation image; and derive the processed second radiation image by removing the derived scattered ray component of the second radiation image from the second radiation image.

3. The radiation image processing device according to claim 2, wherein the processor is configured to derive, for the region of the contrast agent in the second radiation image, the scattered ray component of the second radiation image by correcting the scattered ray component of the first region based on an amount and a density of the contrast agent injected into the tubular structure.

4. The radiation image processing device according to claim 2, wherein the processor is configured to derive, for the region of the contrast agent in the second radiation image, the scattered ray component included in the second radiation image by correcting the scattered ray component of the first region based on a pixel value of the first region.

5. The radiation image processing device according to claim 1, wherein the tubular structure is a blood vessel.

6. The radiation image processing device according to claim 2, wherein the tubular structure is a blood vessel.

7. The radiation image processing device according to claim 3, wherein the tubular structure is a blood vessel.

8. The radiation image processing device according to claim 4, wherein the tubular structure is a blood vessel.

9. A radiation image processing method comprising:

via a computer, acquiring a first radiation image including a tubular structure before an injection of a contrast agent and a second radiation image including the tubular structure during the injection of the contrast agent or after the injection of the contrast agent;

deriving a processed first radiation image by removing a scattered ray component included in the first radiation image;

deriving a processed second radiation image by removing a scattered ray component included in the second radiation image based on the scattered ray component of the first radiation image; and deriving a difference image between the processed first radiation image and the processed second radiation image.

10. A non-transitory computer-readable storage medium that stores a radiation image processing program causing a computer to execute:

a procedure of acquiring a first radiation image including a tubular structure before an injection of a contrast agent and a second radiation image including the tubular structure during the injection of the contrast agent or after the injection of the contrast agent;

a procedure of deriving a processed first radiation image by removing a scattered ray component included in the first radiation image;

a procedure of deriving a processed second radiation image by removing a scattered ray component included in the second radiation image based on the scattered ray component of the first radiation image; and a procedure of deriving a difference image between the processed first radiation image and the processed second radiation image.

* * * * *